United States Patent [19]

Baumbach

[11] 4,425,118
[45] Jan. 10, 1984

[54] CATHETER ADVANCEMENT AND PLACEMENT UNIT

[76] Inventor: James W. Baumbach, 11554 Encino Ave., Granada Hills, Calif. 91344

[21] Appl. No.: 412,704

[22] Filed: Aug. 30, 1982

[51] Int. Cl.$^3$ .............................................. A61M 5/00
[52] U.S. Cl. .................................................. 604/164
[58] Field of Search ................ 604/164, 165, 166–170, 604/136, 192, 197, 198, 263

[56] References Cited

U.S. PATENT DOCUMENTS

| | | | |
|---|---|---|---|
| 3,348,544 | 10/1967 | Braun | 604/164 |
| 3,714,945 | 2/1973 | Stanley | 128/214.4 |
| 3,859,998 | 1/1975 | Thomas | 128/214.4 |
| 4,191,186 | 3/1980 | Keeler | 604/164 |
| 4,193,400 | 3/1980 | Palmer | 128/214.4 |
| 4,292,970 | 10/1981 | Hession, Jr. | 604/164 X |
| 4,369,186 | 5/1982 | Loveless et al. | 128/214.4 |

Primary Examiner—Stephen C. Pellegrino
Attorney, Agent, or Firm—William H. Maxwell

[57] ABSTRACT

A catheter placement unit for initial exposure of a stylet point and subsequent shifting of the catheter to a predetermined position coextensively overlying the point, by a manually operable lever disposed to one side of the unit in relation to the rotative position of the point and exposing the flashback chamber thereof.

13 Claims, 4 Drawing Figures

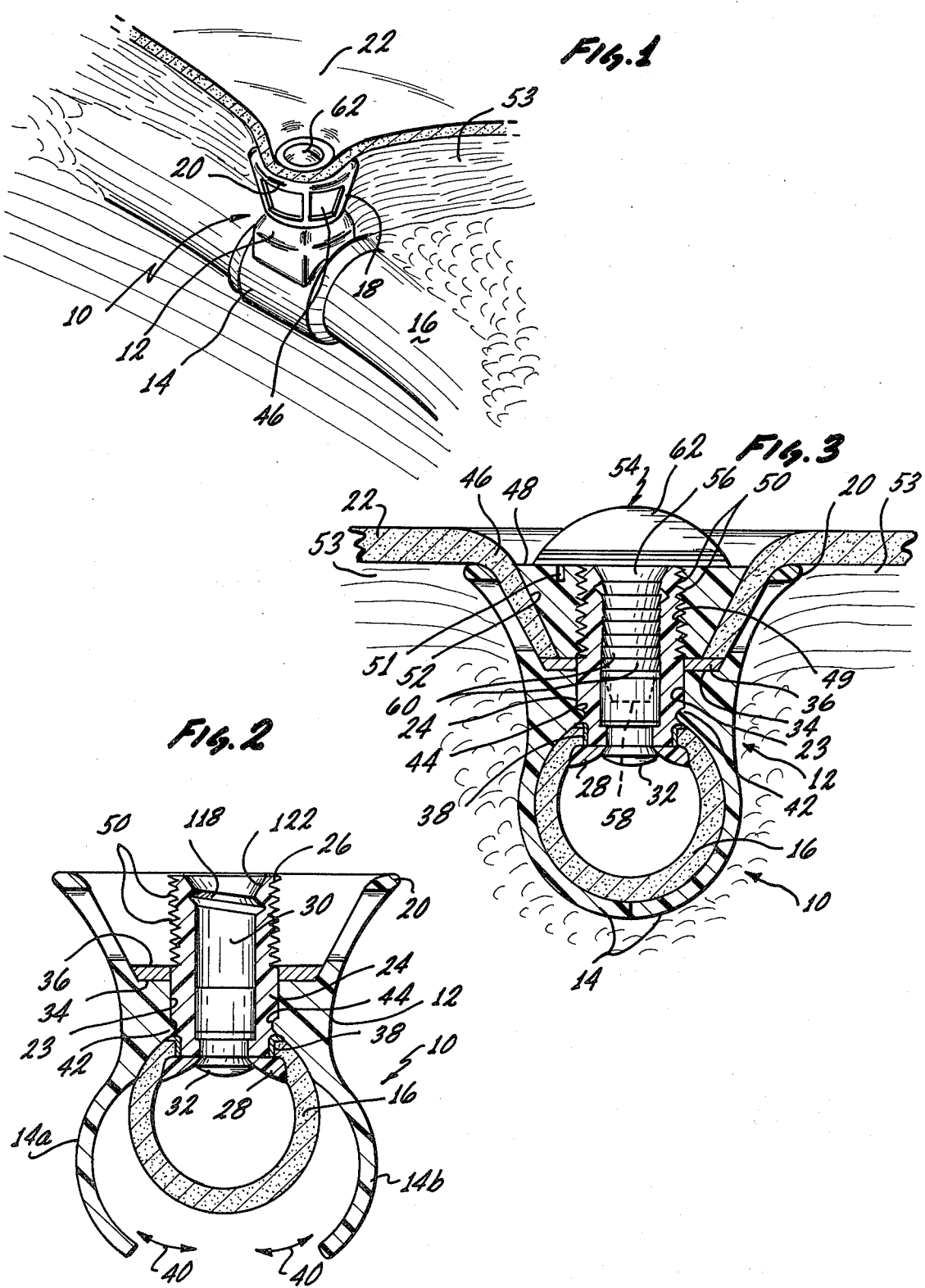

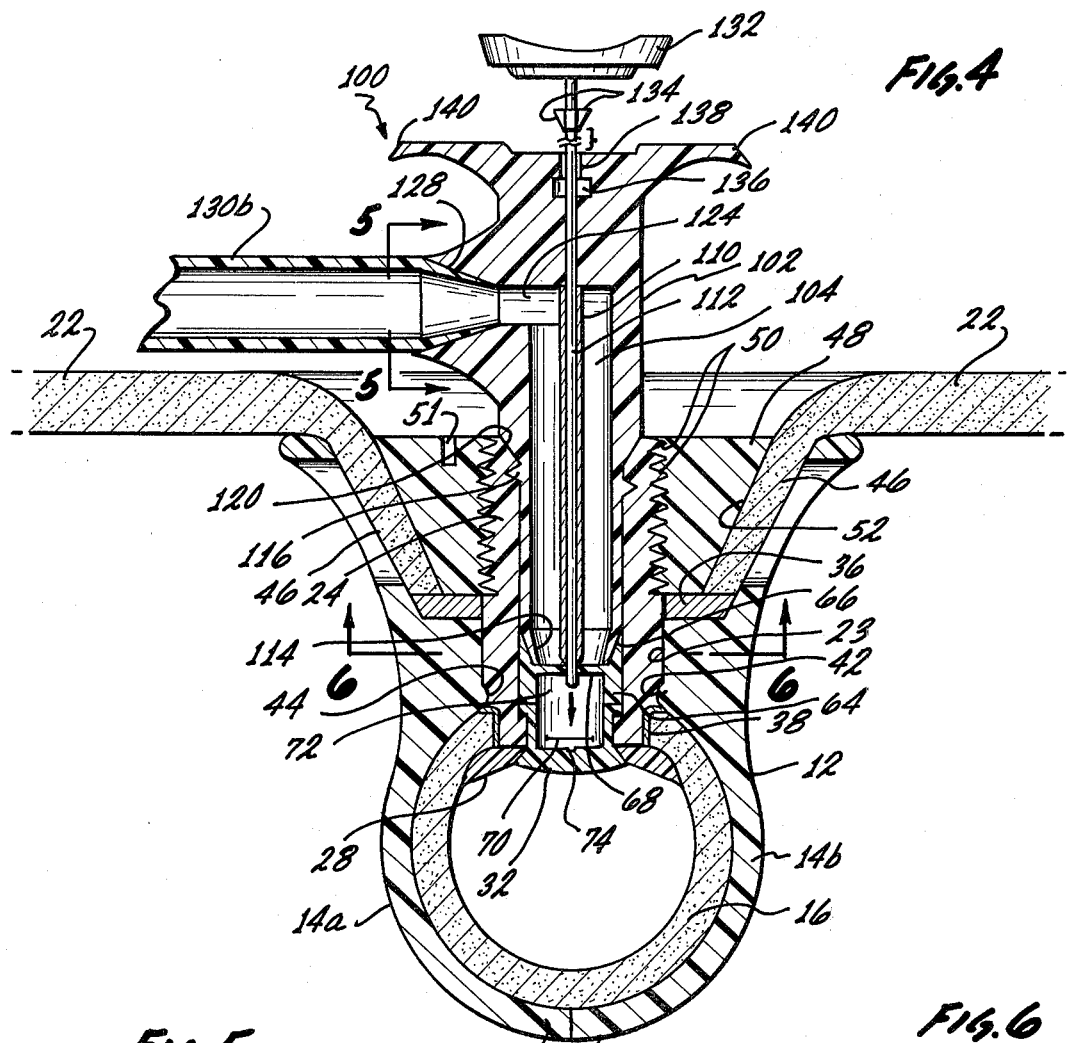
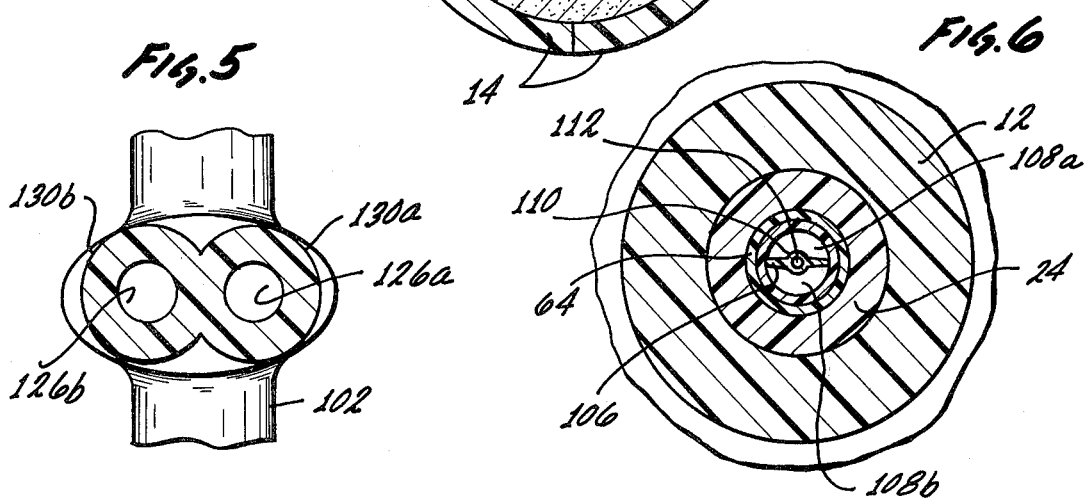

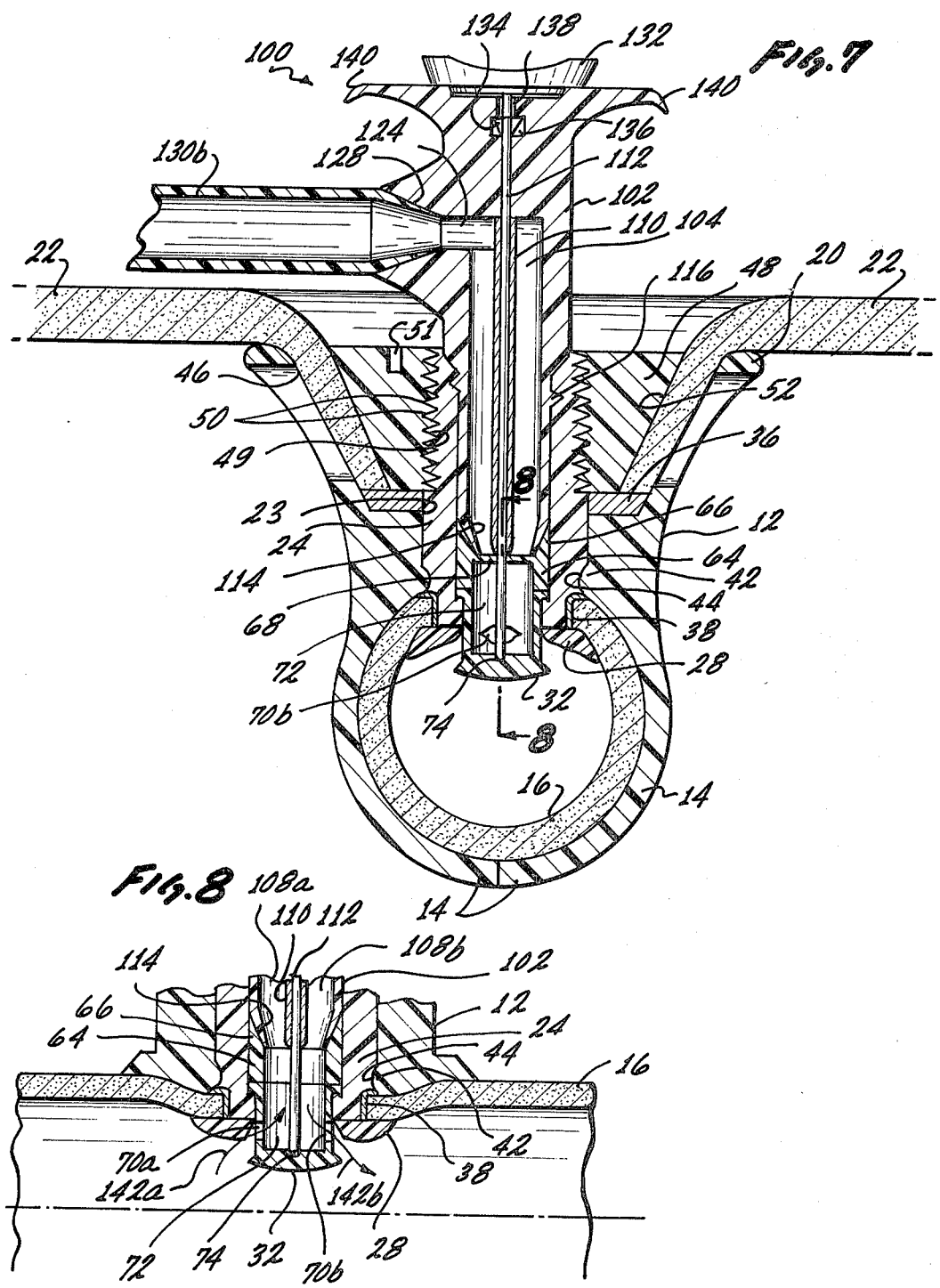

CATHETER ADVANCEMENT AND PLACEMENT UNIT

BACKGROUND

This invention relates to cannula insertion and to the exposure of, and to the subsequent protected relationship of, and following separation of, a stylet from a catheter.

The combination of a stylet and catheter for cannula insertion is well known as a "Catheter Placement Unit", and requires certain procedures and precautions in order to ensure communication into the intravascular space without puncturing the opposite wall of the blood vessel. The stylet functions to puncture the skin, subcutaneous tissue and blood vessel, when the catheter is retracted from the point of the stylet. The catheter is a tubular sleeve slidably engaged over the stylet to protect and reinforce the same, normally retracted a sufficient distance to expose only the truncated point of the tubular stylet. The catheter interior closely fits the stylet exterior, and its distal portion is conically tapered, for ease of entry into the punctured opening established by the stylet. It is for this purpose that the skin of the patient is tensioned through traction by one hand of the operator to prevent tissue and vessel displacement when the catheter placement unit is introduced.

Insertion of the catheter placement unit is to be executed by one hand of the operator, who advances the exposed point of the stylet through the skin and tissue and into the lumen of the vessel to be communicated with. During this step of the procedure, the flashback chamber of the stylet hub must be observed for filling with blood which indicates that the stylet point has entered the intravascular space, from which position the point may be moved ahead slightly but not to puncture the opposite wall of the vessel. It is from this condition that the catheter is to be advanced to cover the stylet coextensively, thereby to assure obscurity of the point thereof.

Following the aformentioned step of cannula insertion, the catheter must be advanced sufficiently to ensure reliable intravascular communication. This is safely achieved only when the point of the stylet is faithfully covered by the catheter tube, it being an object of this invention to ensure this protection by mechanical means having a definite and positive rule of action. Heretofore, such devices have not been infalible, and on the contrary have been entirely dependent upon the expertise of the operator and his best judgement as to position of the stylet point as related to the surrounding catheter tube. With the present invention this positioned relationship is accurately predetermined by a lever means.

Subsequent to the reliable insertion of the catheter tube to the desired depth of penetration, the stylet is withdrawn from the catheter and its hub and is disposed of, as it is an expendable item. The catheter is then ready for intravenous connection as circumstances require, it being an object of this invention to provide for the complete removal of the stylet and its hub and related features such as an air bleed plug and the like, and including the lever feature which characterizes this invention.

The foregoing catheter or insertion proceedure has depended greatly upon the expertise of the operator and his dexterity, and the highly skilled operator can complete the process only with difficulty; others often resort to freeing the first mentioned "one hand" from its traction capability, thereby subjecting the process to elastic recoil of the skin and likely displacement of the stylet the intravascular space often resulting in failure to properly place the catheter. It is an object of this invention to provide means by which one hand of the operator is reserved to the application of traction, and the other hand of the operator is reserved to operation of the catheter placement unit. With the present invention, the catheter placement and lever unit is manipulatable by the said single other hand of the operator.

There have been attempts at complex spring loaded trigger actuated devices for cannula insertion, but with traumatizing results and hazards. Such devices have therefore been unsuccessful, since a discrete and sensible application of such devices is not attainable. Accordingly, it is an object of this invention to provide means by which the operator can sense the position of the stylet catheter, and so that he can sensibly operate the lever means provided herein to effect a predetermined and positive correlationship of the catheter and stylet, and so that a tear or rupture of the vessel wall is precluded.

A functional requirement of the operator is to know of the rotative orientation of the stylet point truncation. That is, it is usually preferred that the truncation plane of the stylet point be faced upwardly; and that disposition can be related to the rotative position of features on the hub of the stylet. Accordingly, it is an object of this invention to position the lever means with respect to the position of said truncation. This angular displacement is preferably 90°, in order to realize a further objective of providing visual contact with the flashback chamber of the stylet hub. As a result, whether manipulated right or left handedly, the flashback chamber is always visible to the operator, since the lever operates in a plane 90° to plane of truncation facing the operator. In practice, the lever is disposed to the right of the truncation plane for right handed operation. Left handed operators have two alternatives, one to employ the unit as disposed for a right handed person, and the other to revolve the unit 180° so that the truncation plane is reversed. In either case, the flash chamber is visibly exposed.

The prior art has provided means for the expert operator to position the catheter to the stylet according to his best judgement, but not measurable to an exact relationship. In other words, no positive placement has been provided for, in which case the relative positions of the catheter and stylet have been conjecture and debatable, as a matter of fact in each instance of application. Therefore, it is an object of this invention to make the catheter and stylet relationship known in each instance, and particularly during deep penetration of the catheter into the intravascular space.

With the present invention, the catheter hub is freely rotatable, there are no extra devices connected to the catheter per se, and there are no disadvantageous modifications to the stylet and its flashback chamber and/or bleed plug. The lever system which characterizes this invention does not obstruct the flashback chamber, and does not encumber the catheter placement unit as such. It is by a simple pivot means that the lever means is attached to the stylet hub, and through this installation the catheter is positively shifted from an initial position where the stylet point is exposed, to a protective position where the stylet point is withdrawn and obscured.

SUMMARY OF THE INVENTION

This invention is concerned with cannula insertion of catheters for intravenous liquid application, and involves the use of a stylet to make penetration into the intravascular space. The catheter remains unaltered and the stylet is preferably modified but slightly, but in no sense to encumber the same. Characteristically, this invention provides a lever means disposed between the catheter hub and stylet hub, and operable through a limited angular displacement to shift the catheter forwardly a predetermined distance so as to cover the stylet point. Conversely, so long as the catheter remains retracted, prior to operation of the lever means, the stylet point is exposed for penetration. In practice, the lever means is secured by a pivot to the stylet hub, at one side thereof on a vertical axis when the truncation of the stylet point is rotated to face upwardly. There is but one lever part added to the usual catheter placement unit, and a pivot means is preferably applied to the stylet hub, and all of which is easily fabricated of plastic material according to usual practice, as will be described.

The foregoing and various other objects and features of this invention will be apparent and fully understood from the following detailed description of the typical preferred form and application thereof, throughout which description reference is made to the accompanying drawings.

THE DRAWINGS

PREFERRED DESCRIPTION

Figure 1:
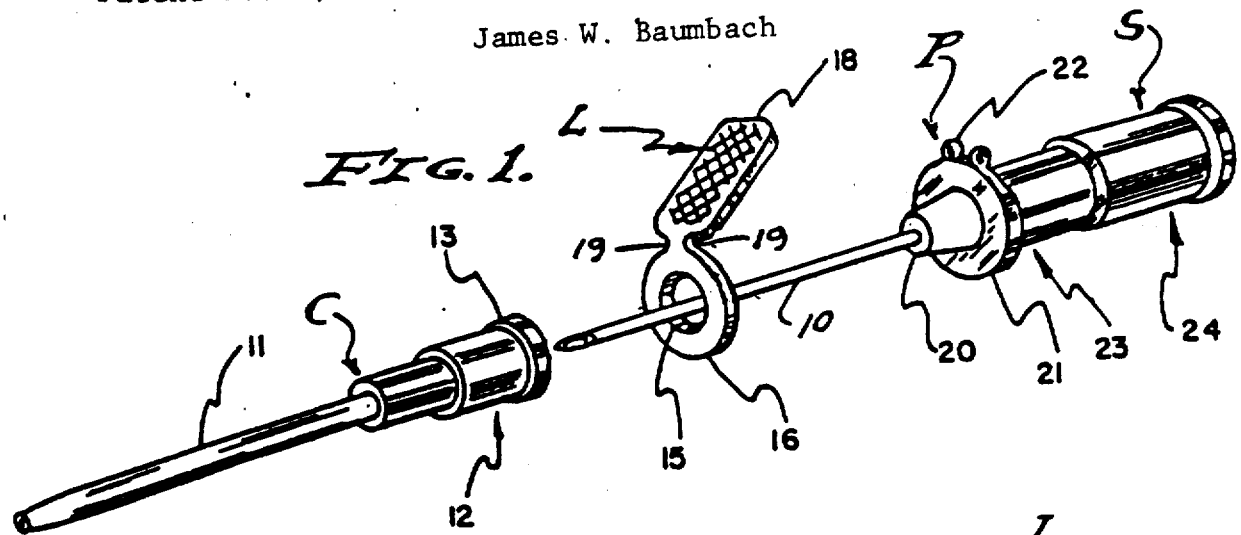
FIG. 1 is an exploded perspective view of the catheter placement unit of the present invention, with the lever means shown as it is disposed between the catheter hub and stylet hub.

Referring now to the drawings, this invention involves generally a stylet S, a catheter C, and a lever means L and pivot means P therefor.

The stylet S is a hypodermic unit comprised of a tubular needle 10 carried at its base by a hub 20 surrounded by an adjacent flange 21. The hub is tapered forwardly to telescopically engage with the hub of the catheter, and it carries a rearward extention or flashback chamber 23 of cylindrical configuration. An air bleed plug 24 slides forwardly within and over the cylinder of chamber 23, the latter being made of transparent material for the observation of blood entering therein. The needle 10 is of the usual form carried through a bore in hub 20 so as to open into chamber 23 and with a truncated distal end forming a sharpened point. The stylet thus far described is conventional in every respect.

The catheter C is a cannula unit comprised of a tubular sleeve 11 carried by a hub 12 and formed to telescopically engage over the aforementioned stylet needle 10. The interior of the hub 12 is tapered to frictionally engage with the taper on the extension of the hub 20, whereby the catheter C is releasably mounted to the stylet S. As shown, the distal portion of the catheter sleeve 11 is tapered, to enable entry through an opening made through tissue by the stylet point. The catheter C sleeve 11 exposes the distal truncated and sharpened end portion of the needle 10, when it is firmly coupled to the stylet 8 as shown in FIG. 2 with the rear face of the catheter hub 12 positioned closely to the front face of the flange 21 of stylet S, this being the conventional catheter placement unit condition for and cutaneous subcutaneous penetration.

Figure 2:
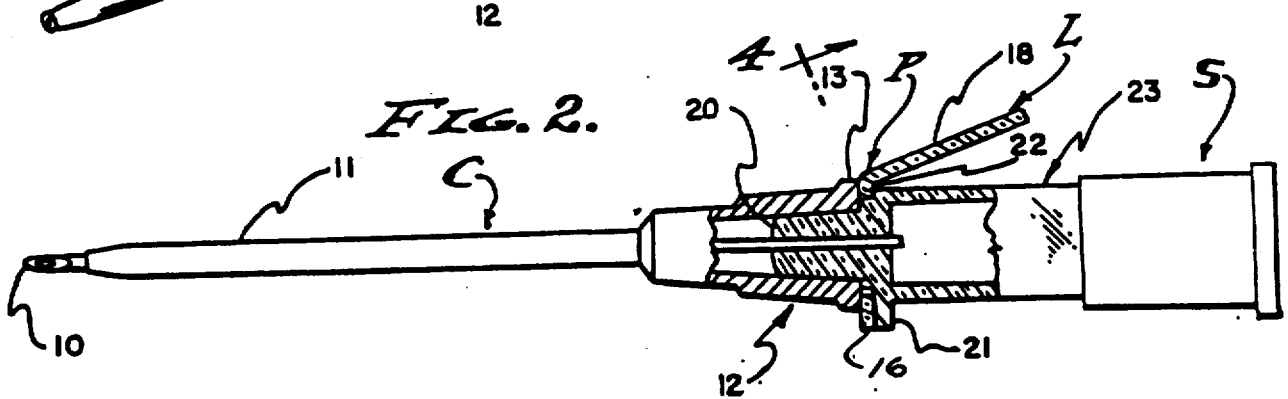
FIG. 2 is an enlarged longitudinal sectional view, showing the catheter and stylet assembled with the lever means unactuated therebetween.
Figure 3:
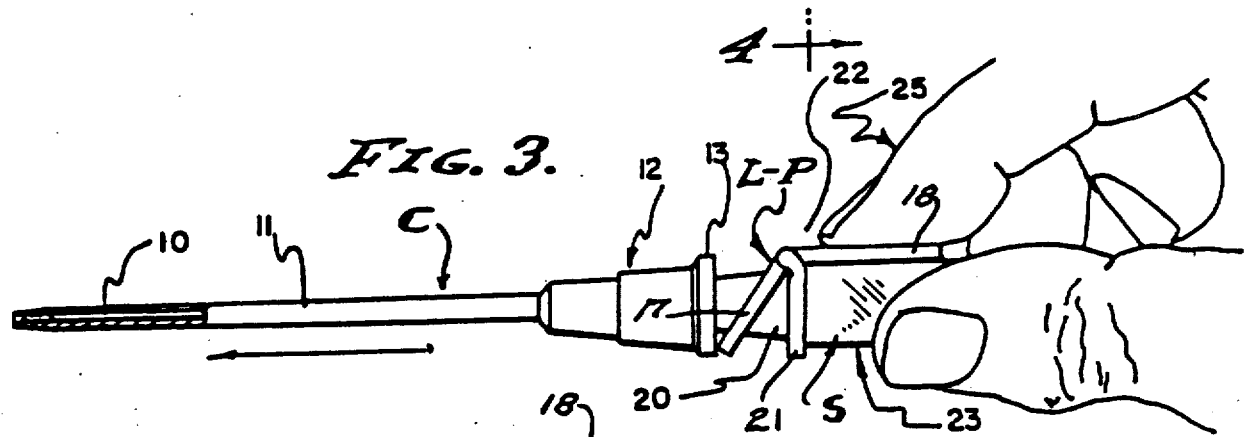
FIG. 3 is a view similar to FIG. 2, showing the unit gripped by the hand of an operator and the lever means connected to advance the catheter to coextensively cover the point of the stylet.

In accordance with this invention, I provide a lever means L by which the catheter C is released from the stylet S and shifted an exact predetermined distance, a distance to coextenively overly the needle 10 of the stylet as shown in FIG. 3. As shown throughout the drawings, the lever means L comprises a first class lever of obtuse configuration having a first leg 16 disposed between the aforesaid faces of the catheter and stylet hubs (see FIG. 2), and a second rearwardly extending leg 18 overlying a side of the flashback chamber 23. The prepared position of leg 16 is in a plane normal to the common axis of the stylet and catheter. There is a fulcrum at the joinder of legs 16 and 18, to occur at the periphery of flange 21, whereby depression of leg 18 angularly displaces the leg 16 which thereby forces the separation of the catheter hub 12 from the stylet hub 20 so as to move the catheter forwardly as shown in FIG. 3. As shown, the leg 18 is knurled for non-slip finger engagement. This movement of the catheter is restricted by the limited movement of leg 18 that stops against the side of the flashback chamber 23 (see FIG. 3).

The lever means L can be secured to the catheter placement unit in various ways, with the leg 16 embraced and/or clamped between the hubs 12 and 20 as best illustrated in FIG. 2. As shown of FIG. 1, the lever 16 is shaped to the same diameter as the largest of the two hubs, and in practice to the diameter of flange 21, and with a bore 15 therethrough of substantially greater diameter than the base portion of the hub 12 that it surrounds the periphery 17 of leg 16 conforms in diameter to the hub flange 21, as shown in FIGS. 1 and 2. It is by this surrounding configuration that the lever means L is captured to the catheter placement unit, is permitted to pivot, and cannot be lost prior to the operation of shifting the catheter over the stylet needle.

Figure 4:
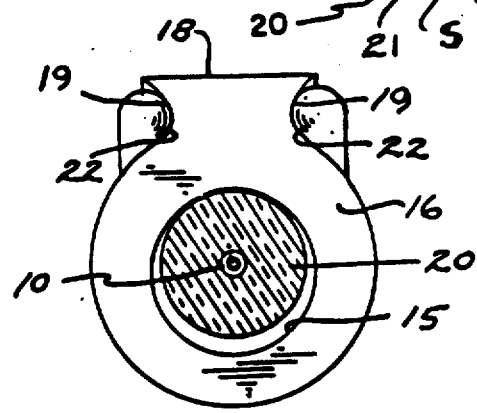
FIG. 4 is an enlarged detailed sectional view of the pivot means and taken substantially as indicated by line 4—4 on FIG. 2.

In its preferred form, the lever means L is captured to the stylet S by pivot means P, and so that the lever means has a known axially rotative position with respect to the stylet point. In practice, the axis of pivot means P is vertically disposed to the right side of the flange 21 when the truncated plane of the needle point is faced upwardly. A feature is that the lever means L snaps onto the stylet flange 21 in the aforementioned position, preferably by means of spaced lugs 22 having opposed semi-spherical faces engageable into complementary semi spherical sockets 19 at opposite sides of the fulcrum of the two legs 16 and 18 (see FIGS. 1 and 4). The lever legs 16 and 18 are displaced substantially 110° so that the angular displacement of leg 16 is 20°, as shown herein, and sufficient for travel of the catheter sleeve 11 to assuredly cover the point of needle 10.

From the foregoing it will be seen that the catheter C can be deftly moved to cover the point of the stylet S, simply by manipulating the lever means L with one finger 25, preferably the index finger, while the several remaining fingers are in gripped engagement with the stylet flashback chamber as clearly shown in FIG. 3. Movement of the index finger 25 does not affect unit placement by the other fingers, for example the thumb and middle finger of the hand. Thus, needle position is not affected when advancing the catheter to an exact position for its subsequent deep penetration into the intravascular space, during which penetration exposure of the needle point is precluded. The lever means L remains intact with the stylet unit and is disposed of therewith.

Having described only a typical preferred form and application of my invention, I do not wish to be limited or restricted to the specific details herein set forth, but wish to reserve to myself any modifications or variations that may appear to those skilled in the art as set forth within the limits of the following claims.

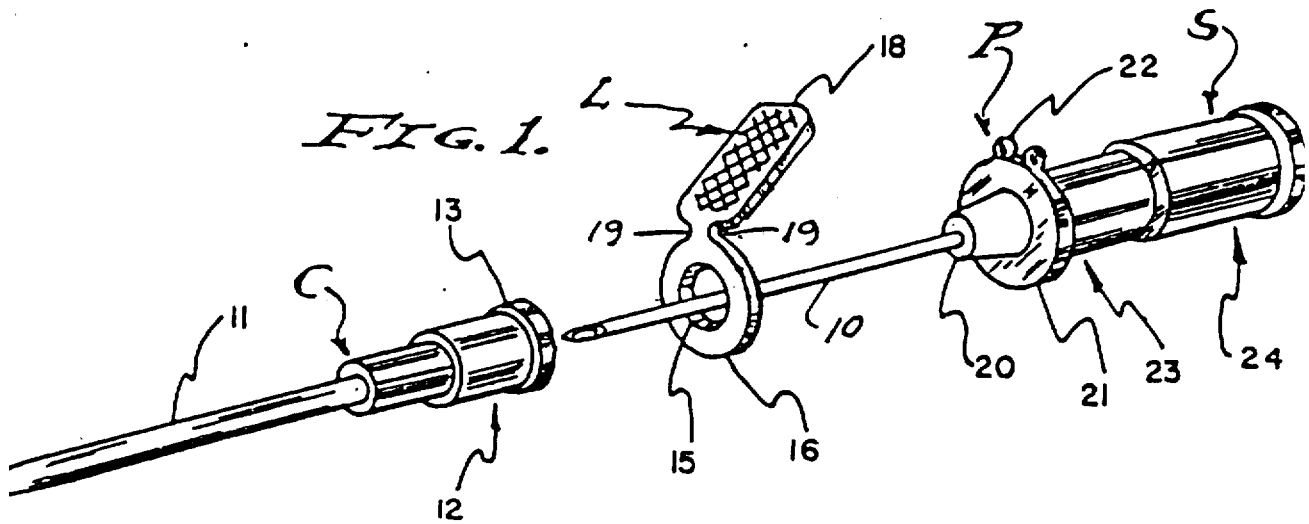

I claim:

1. A catheter placement unit comprised of a catheter removably engaged over a stylet;
    the stylet being comprised of a tubular needle sharpened at its forward distal end and carried at its base end by a hub with a forwardly faced flange and a rearward extension,
    the catheter being comprised of a tubular sleeve slideably engageable over the stylet needle and having a hub with a rearwardly disposed face opposed to the forwardly faced flange of the stylet,
    there being lever means with a fulcrum at a side of the unit and engaged between the forwardly faced flange of the stylet hub and the rearwardly disposed face of the catheter hub and manually operable into stopped engagement with said rearward extension to shift the catheter into coextensive placement over the stylet needle and point thereof.

2. The catheter placement unit as set forth in claim 1, wherein the lever means has a leg with a bore loosely engaged over the stylet hub and disposed between the forwardly faced flange of the stylet hub and the rearwardly disposed face of the catheter hub.

3. The catheter placement unit as set forth in claim 1, wherein the lever means has a first leg engaged between the forwardly faced flange of the stylet hub and the rearwardly disposed face of the catheter hub, and has a second leg extending rearwardly at the side of the rearward extension of the stylet hub to have stopped engagement therewith to angularly position said first leg for predetermined movement.

4. The catheter placement unit as set forth in claim 1, wherein the lever means has a first leg with a bore loosely engaged over the stylet hub and disposed between the forwardly faced flange of the stylet hub and the rearwardly disposed face of the catheter hub, and a second leg extending rearwardly at the side of the rearward extension of the stylet hub to have stopped engagement therewith to angularly position said first leg for predetermined movement.

5. The catheter placement unit as set forth in any one of claims 1, 2, 3 or 4, wherein pivot means secures the lever means to the side of the unit.

6. The catheter placement unit as set forth in any one of claims 1, 2, 3 or 4, wherein pivot means secures the lever means to the flange of the stylet hub at the side of the unit.

7. The catheter placement unit as set forth in any one of claims 1, 2, 3 or 4, wherein the lever means is snapped onto pivot means comprised of opposed lugs engageable into opposite sockets in the fulcrum of the lever means.

8. The catheter placement unit as set forth in any one of claims 1, 2, 3 or 4, wherein the lever means is snapped onto pivot means comprised of opposed lugs with seal spherical faces engaged into opposite semi spherical sockets in the fulcrum of the lever means.

9. The catheter placement unit as set forth in any one of claims 1, 2, 3 or 4, wherein pivot means is disposed on a vertical axis related to a horizontal truncation that forms the needle point and secures the lever means to the side of the unit, whereby the rearward extension of the stylet hub is upwardly visible.

10. The catheter placement unit as set forth in any one of claims 1, 2, 3 or 4, wherein pivot means is disposed on a vertical axis related to an upwardly faced horizontal truncation that forms the needle point and secures the lever means to the side of the unit, whereby the rearward extension of the stylet hub is upwardly visible.

11. The catheter placement unit as set forth in any one of claims 1, 2, 3 or 4, wherein pivot means is disposed on a vertical axis at the right side of the unit and related to a horizontal truncation that forms the needle point and secures the lever means to the side of the unit, whereby the rearward extension of the stylet hub is upwardly visible.

12. The catheter placement unit as set forth in any one of claims 3 or 4, wherein the first and second legs of the lever means are obtusely related.

13. The catheter placement unit as set forth in any one of claims 3 or 4, wherein the first and second legs of the lever means are obtusely separated at substantially 110°.

* * * * *

UNITED STATES PATENT AND TRADEMARK OFFICE
CERTIFICATE OF CORRECTION

PATENT NO. : 4,425,118
DATED : January 10, 1984
INVENTOR(S) : James W. Baumbach

It is certified that error appears in the above-identified patent and that said Letters Patent is hereby corrected as shown below:

The title page showing the illustrative figure should be deleted to appear as per attached title page.

In the drawing the three sheets of drawing should be deleted to be replaced with one sheet of drawing as shown on the attached sheet.

Column 4, line 42, should read as follows:

-- surrounds. The periphery 17 of leg 16 conforms in diame- --.

Signed and Sealed this

Twenty-fifth Day of September 1984

[SEAL]

Attest:

GERALD J. MOSSINGHOFF

Attesting Officer

Commissioner of Patents and Trademarks

United States Patent [19]

Baumbach

[11] 4,425,118
[45] Jan. 10, 1984

[54] CATHETER ADVANCEMENT AND PLACEMENT UNIT

[76] Inventor: James W. Baumbach, 11554 Encino Ave., Granada Hills, Calif. 91344

[21] Appl. No.: 412,704

[22] Filed: Aug. 30, 1982

[51] Int. Cl.³ .................................................. A61M 5/00
[52] U.S. Cl. ................................................................ 604/164
[58] Field of Search ............... 604/164, 165, 166–170, 604/136, 192, 197, 198, 263

[56] References Cited

U.S. PATENT DOCUMENTS

| | | | |
|---|---|---|---|
| 3,348,544 | 10/1967 | Braun | 604/164 |
| 3,714,945 | 2/1973 | Stanley | 128/214.4 |
| 3,859,998 | 1/1975 | Thomas | 128/214.4 |
| 4,191,186 | 3/1980 | Keeler | 604/164 |
| 4,193,400 | 3/1980 | Palmer | 128/214.4 |
| 4,292,970 | 10/1981 | Hession, Jr. | 604/164 X |
| 4,369,186 | 5/1982 | Loveless et al. | 128/214.4 |

*Primary Examiner*—Stephen C. Pellegrino
*Attorney, Agent, or Firm*—William H. Maxwell

[57] ABSTRACT

A catheter placement unit for initial exposure of a stylet point and subsequent shifting of the catheter to a predetermined position coextensively overlying the point, by a manually operable lever disposed to one side of the unit in relation to the rotative position of the point and exposing the flashback chamber thereof.

13 Claims, 4 Drawing Figures